United States Patent [19]

Tesmann et al.

[11] Patent Number: 4,702,823
[45] Date of Patent: Oct. 27, 1987

[54] PHOSPHINIC ACID ADDUCTS WITH MALEIC ACID SEMIESTERS, A PROCESS FOR THEIR PRODUCTION AND THEIR USE

[75] Inventors: Holger Tesmann; Helmut Blum, both of Duesseldorf; Rita Koester, Neuss, all of Fed. Rep. of Germany

[73] Assignee: Henkel Kommanditgesellschaft auf Aktien, Duesseldorf, Fed. Rep. of Germany

[21] Appl. No.: 879,716

[22] Filed: Jun. 27, 1986

[30] Foreign Application Priority Data

Jun. 27, 1985 [DE] Fed. Rep. of Germany ....... 3522930

[51] Int. Cl.$^4$ .............................................. B03D 1/02
[52] U.S. Cl. ....................................... 209/166; 252/61
[58] Field of Search ................... 209/166, 167; 252/61

[56] References Cited

U.S. PATENT DOCUMENTS

| | | | |
|---|---|---|---|
| 4,081,363 | 3/1978 | Grayson | 209/166 |
| 4,138,350 | 2/1979 | Wang et al. | 252/61 |
| 4,139,482 | 2/1979 | Holme | 252/61 |
| 4,192,739 | 3/1980 | Wang et al. | 209/166 |

FOREIGN PATENT DOCUMENTS

| | | | |
|---|---|---|---|
| 390835 | 12/1973 | U.S.S.R. | 209/166 |
| 860866 | 9/1981 | U.S.S.R. | 209/166 |

OTHER PUBLICATIONS

Zhurnal Obshchei Khimii, vol. 45, No. 2, pp. 314–316, 2/85.

*Primary Examiner*—S. Leon Bashore
*Assistant Examiner*—Thomas M. Lithgow
*Attorney, Agent, or Firm*—Ernest G. Szoke; Henry E. Millson, Jr.

[57] ABSTRACT

The invention relates to adducts of phosphinic acid with maleic acid semiesters and salts thereof corresponding to the following general formula

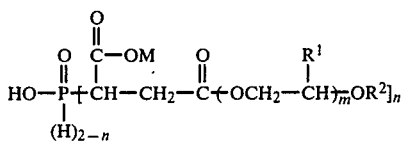

in which
R$^1$ is hydrogen or a methyl group,
R$^2$ is a linear or branched, optionally hydroxyl substituted C$_8$–C$_{18}$ alkyl or cycloalkyl group or an aryl group corresponding to the formula

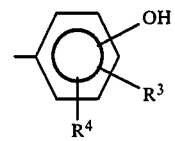

in which
R$^3$ and R$^4$ may be the same or different and are hydrogen or a linear or branched unsubstituted C$_7$–C$_{12}$ alkyl group,
M is H, Na, K or NH$_4$,
m is an integer of from 1 to 8, and
n is 1 or 2.

The invention also relates to a process for production of the adducts and to their use for the flotation of non-sulfidic minerals.

5 Claims, No Drawings

PHOSPHINIC ACID ADDUCTS WITH MALEIC ACID SEMIESTERS, A PROCESS FOR THEIR PRODUCTION AND THEIR USE

BACKGROUND OF THE INVENTION

1. Field of the Invention

This invention relates to adducts of phosphinic acid with maleic acid semiesters, to a process for their production and to their use as flotation aids.

2. Description of Related Art

There are many known processes for the concentration of valuable non-sulfidic (i.e. sulfide free) minerals from size-reduced crude ores by flotation. Examples of these valuable minerals include apatite, fluorite, scheelite and other salt-like minerals, cassiterite and other heavy-metal oxides, for example those of titanium and zirconium, and also certain silicates and alumosilicates which are floated in the presence of collectors. According to "Ullmanns Enzyklopadie der technischen Chemie", Verlag Chemie, Weinheim (1972), Vol. 2, page 115, collectors are organic compounds which generally carry one chemically active polar group on a more or less long hydrocarbon chain. Fatty acids, particularly unsaturated fatty acids, preferably oleic acid, are frequently used as collectors. Other suitable collectors are, for example, sulfonate surfactants (such as alkylaryl sulfonates) or alkyl or aryl phosphonates.

Sulfosuccinic acid monoalkyl esters and sulfosuccinic acid aspartates are proposed as collectors in U.S. Pat. Nos. 4,138,350 and 4,139,482. However, collectors such as these, which are based on fatty acids or sulfonates, are comparatively non-selective because they also float silicate- and carbonate-containing minerals and accordingly can only be used to a limited extent if such minerals accompany other valuable minerals and are to be separated therefrom. Accordingly, other aids, for example so-called "depressors", have to be added to prevent the flotation of unwanted gangues. The resulting mixtures of reagents for flotation have a very complex composition. The selective flotation of valuable non-sulfidic minerals in the presence of calcite as gangue represents a particular technical problem for which fatty acids and collectors containing sulfo groups are not sufficiently suitable in practice.

U.S. Pat. No. 4,430,238 describes dicarboxylic acid semiesters esterified with acylated alkylene oxides, for example maleic acid semiesters esterified with fatty acid acylated alkylene oxides and their use as collectors for the flotation of oxide or salt-like minerals. However, the disadvantage of these compounds is that they are also not sufficiently selective in practice and accordingly necessitate the additional use of other modifying reagents.

DESCRIPTION OF THE INVENTION

Other than in the operating examples, or where otherwise indicated, all numbers expressing quantities of ingredients or reaction conditions used herein are to be understood as modified in all instances by the term "about."

The object of the present invention is to provide new compounds which are easy to prepare, show high solubility in water and are suitable as selective collectors in the flotation of valuable non-sulfidic minerals.

It has been found, surprisingly, that reaction products of phosphinic acid with certain maleic acid semiesters based on alkyl or alkylphenol polyglycol ethers and water-soluble salts thereof show particularly good properties as collectors for valuable non-sulfidic minerals. Accordingly, the present invention relates to adducts of phosphinic acid with maleic acid semiesters and salts thereof corresponding to the following general formula

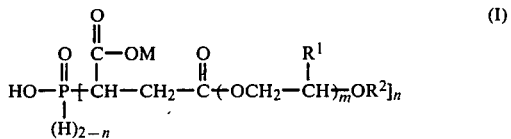

in which
$R^1$ represents hydrogen or a methyl group,
$R^2$ represents an unsubstituted or hydroxyl substituted $C_8$–$C_{18}$ linear or branched alkyl or cycloalkyl group or an aryl group corresponding to the following formula

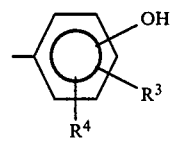

in which
$R^3$ and $R^4$ may be the same or different and represent hydrogen or a linear or branched unsubstituted $C_7$–$C_{12}$ alkyl group,
M is H, Na, K or $NH_4$,
m is an integer of from 1 to 8, and
n is 1 or 2.

The present invention also relates to a process for the production of these adducts of phosphinic acid with maleic acid semiesters and salts thereof corresponding to general formula (I) above in which $R^1$, $R^2$, $R^3$, $R^4$, M, m and n are as defined above, wherein compounds corresponding to the general formula $R^2OH$ are reacted in a molar ratio of 1:m with an epoxide corresponding to the following formula

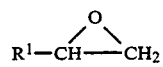

and the resulting alkyl or alkylphenol polyglycol ethers are reacted with maleic acid anhydride in a molar ratio of 1:1 to form maleic acid semiesters; the maleic acid semiesters thus formed being converted, if desired, into the corresponding sodium, potassium or ammonium salts, and phosphinic acid is added to the resulting compounds in a molar ratio of ester to phosphinic acid of 1:1 or 2:1, to obtain adducts corresponding to general formula (I).

The present invention also relates to the use of the above-described adducts corresponding to general formula (I), in which $R^1$, $R^2$, $R^3$, $R^4$, M, m and n are as defined above, in quantities of from 10 to 5000 g/t ore as collectors for the flotation of valuable non-sulfidic minerals.

The adducts of phosphinic acid (which is tautomeric with hypophosphorous acid) with maleic acid semiesters may be either monoadducts, i.e. adducts of a phosphinic acid molecule with the double bond of a maleic acid semiester molecule, or diadducts, i.e. adducts of a phosphinic acid molecule with the double bonds of two maleic acid semiester molecules or mixtures thereof. In the production of the adducts on a pilot plant or industrial scale, mixtures of 1:1- and 1:2-adducts are generally obtained and may either be separated from one another by known methods or they may be used in the form of their mixtures as collectors for the flotation of valuable non-sulfidic minerals.

The $R^2$ substituents on the adducts of general formula (I) according to the invention may be linear or branched $C_8$–$C_{18}$ alkyl or cycloalkyl groups and these groups may be substituted by a hydroxyl group. Examples of such substituents are the residues of naturally occurring fatty alcohols which generally contain an even number of C-atoms, such as octanol, decanol, dodecanol, tetradecanol, etc. However, alcohols containing branched alkyl chains or an odd number of C-atoms may also be used. $R^2$ preferably is a $C_{12}$–$C_{16}$ alkyl group.

However, $R^2$ may also be an aryl group corresponding to the following general formula

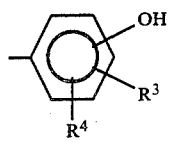

preferably where $R^3$ represents hydrogen and $R^4$ represents an unsubstituted $C_7$–$C_{12}$ alkyl group or both $R^3$ and $R^4$ represent unsubstituted $C_7$–$C_{12}$ alkyl groups. The alkyl groups $R^3$ and/or $R^4$ preferably contain from 8 to 12 C-atoms.

In general formula (I), the substituent $R^2$ is preferably a linear decyl or dodecyl group. However, it is also possible on an industrial scale to produce mixtures of compounds corresponding to general formula (I) in which $R^2$ represents alkyl groups of a technical fatty alcohol mixture containing for example from 10 to 18 C-atoms.

The maleic acid semiester moeity contains ester groups containing from 1 to 8 ethoxy or propoxy groups in addition to the alkoxy group just mentioned. From 2 to 4 glycolether groups is preferred. These groups are formed by ethoxylation of the corresponding fatty alcohols or fatty alcohol mixtures using, preferably, 2 to 4 moles of ethylene oxide per mole of alcohol.

The adducts of phosphinic acid with maleic acid semiesters according to the invention are produced in accordance with the following reaction scheme:

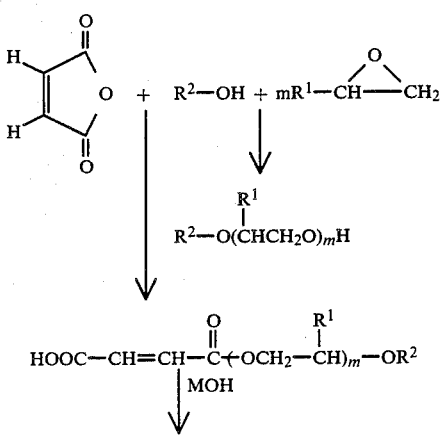

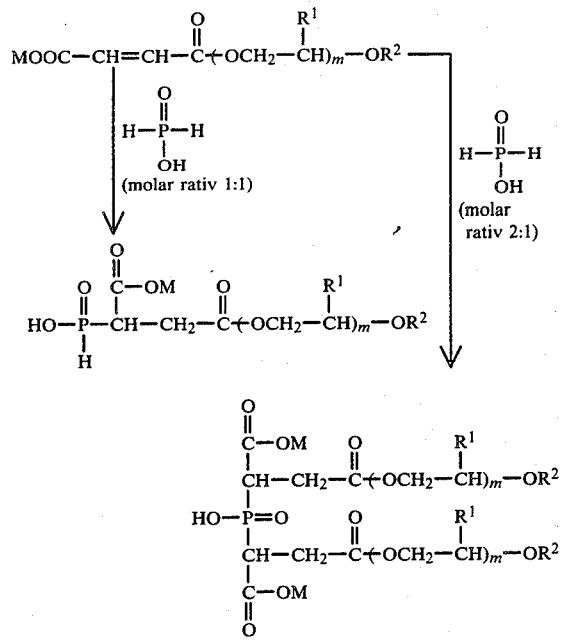

As seen from the above reaction scheme, alcohols or alkylphenols of the general formula $R^2OH$ are reacted with ethylene oxide or propylene oxide in a molar ratio of 1:1–8 to form alkyl or alkylphenol polyglycol ethers, a molar ratio of alcohol to ethylene oxide or propylene oxide of 1:2–4 being preferred. Ethylene oxide is preferably used for the alkoxylation reaction.

The alkyl or alkylphenol polyglycol ethers formed are reacted with maleic acid anhydride in a molar ratio of 1:1 to form the corresponding maleic acid semiesters. This reaction, which takes place under known esterification reaction conditions may be followed by neutralization of the free carboxyl group with basic reactants, for example aqueous alkali metal hydroxide, ammonium hydroxide or carbonate solutions.

The acid or salts of maleic acid semiesters formed are reacted with hypophosphorous acid (phosphinic acid) in a molar ratio of 1:1 or 2:1 in an inert atmosphere at elevated temperature. The reaction is preferably carried out under nitrogen as the inert gas at a reaction temperature of from 90° to 130° C. (sump temperature). To initiate the addition reaction, an inorganic or organic radical former (initiator) is added to the reaction mixture in sub-stoichiometric quantities. An aqueous solution of alkali metal peroxodisulfate, particularly sodium peroxodisulfate, is preferably used. A mixture of the mono- and diadduct of phosphinic acid with the maleic acid semiesters used is formed in this way. The mixture may be separated into its individual components in known manner, although it is preferably used as such as a collector for the flotation of valuable non-sulfidic minerals.

The new adducts according to the invention and their water-soluble salts which are obtained as liquid to viscous products in the form of aqueous mixtures having active substance contents of from 70 to 90%, dissolve readily in water without heating for use as collectors in flotation without any need to add other collectors. Aqueous solutions containing from 10 to 5000 g/t of ore and preferably from 100 to 3000 g/t of ore of the new adducts are used for flotation. The use of the compounds of the invention alone as collectors gives a distinct improvement in selectivity in the recovery of valuable minerals as compared to the collectors known from the prior art, for example the above-mentioned fatty acids or sulfonated maleic acid semiesters.

However, the compounds according to the invention may also be used in combination with so-called co-collectors for further improving output and also the metallurgical results. Co-collectors are flotation collectors known from the prior art from the group comprising anionic surfactants. Examples of co-collectors are fatty acids or derivatives thereof, sulfonation products of fatty oils or alkyl benzenes, sulfosuccinic acid esters and amides, alkylether phosphates, alkylether sulfates and comparable compounds. For each type of mineral to be treated an optimized combination of parameters will be used which the expert can determine with the aid of a few informative preliminary tests.

In addition, other compounds may be added to the flotation medium, depending on the particular dressing problem and the plant requirements. Compounds of this type include pH-regulators, inorganic and organic depressors and other additives known per se, such as frothers for example. In this way, it is possible to even further improve recovery of the valuable mineral using the maleic acid semiester/phosphinic acid adducts of the invention. These additional compounds are of particular relevance when separating ores of relatively low value into valuable material and gangue.

The invention is illustrated by the following Examples:

EXAMPLE 1

Preparation of the adducts of phosphinic acid with maleic acid semiesters according to the invention.

(a) A technical fatty alcohol mixture containing $C_{12}$–$C_{16}$ alcohols was reacted with four equivalents of ethylene glycol to form the corresponding alkyl polyglycol ether. The reaction with maleic acid anhydride in a molar ratio of 1:1 gave the corresponding maleic acid semiester (formula (I): $R^1$=H; $R^2$=$C_{12}$–$C_{16}$ alkyl; m=4).

0.5 Mole of this starting semiester was heated under nitrogen to 90° C., after which 33 g (0.5 mole) of hypophosphorous acid in the form of a 50% aqueous solution was added dropwise. A 12% aqueous solution of 15 g (63.0 moles) sodium peroxodisulfate was then added dropwise at the same temperature. The mixture was then heated for 2 hours to 100° C. and thereafter to a sump temperature of 130° C. Approximately 100 ml of water was distilled off, leaving a homogeneous, thick liquid product which, according to $^{31}$P-NMR-spectroscopic analysis, contained the mono- and diadduct of the hypophosphorous acid with the starting maleic acid semiester (formula (I): n=1 and 2).

(b) To prepare another adduct mixture, the starting material used was a maleic acid semiester of which the alcohol component had been obtained from an adduct of 4 moles of ethylene oxide with a technical mixture of $C_{10}$–$C_{18}$ fatty alcohols (0 to 3% $C_{10}$; 48 to 58% $C_{12}$; 19 to 24% $C_{14}$; 9 to 12% $C_{16}$ and 10 to 14% $C_{18}$). The semiester was obtained by reaction of the alcohol component with maleic acid anhydride in a molar ratio of 1:1.

145.2 g (0.6 mole) of this maleic acid semiester mixture was heated under nitrogen to 90° C. before 39.6 g (0.6 mole) hypophosphorous acid in the form of a 50% aqueous solution was slowly added. A solution of 9 g (37.8 moles) of sodium peroxodisulfate in 60 ml water was then added dropwise at the same temperature. The reaction mixture was then heated for 2 hours to 100° C. and thereafter to a sump temperature of 130° C. with removal by distillation of 70 ml water. The reaction product obtained in this way contained 5.2% by weight of phosphorus. According to analysis by $^{31}$P-NMR-spectroscopy, the reaction product contained (based on the quantity of hypophosphorous acid used) from 25 to 30% of the phosphorus used as monoadduct (formula (I); n=1) ($\delta$p=29.13 ppm) and from 10 to 15% of the phosphorus used as diadduct (formula (I); n=2) ($\delta$p=36.71 ppm). In addition, unreacted hypophosphorous acid ($\delta$p=7.74 ppm) and phosphorous acid formed by oxidation ($\delta$p=4.93 ppm) were detected to which the remaining phosphorus in the reaction product was attributed.

EXAMPLE 2

Flotation using the adduct mixtures of the invention.

The arrangement used for the flotation tests consisted of a modified "Hallimond tube" according to B. Dobias in "Colloid and Polymer Sci." 259, 775 to 776 (1981), which had a volume of 160 ml. The apparatus was charged with 1.5 g of a ground ore (see below) and a solution of the collector (28 mg/l active substance, corresponding to 3000 g/t). A valuable mineral concentrate was discharged through the flotation medium and was analyzed as a function of time.

The mineral sample consisted of apatite from a sedimentary deposit with a high content of calcite as gangue, in which the following constituents were quantitatively determined: 23.5% $P_2O_5$, 53.0% CaO, 16.3% $CO_2$, 2.5% $F^-$, 1.9% $SiO_2$.

The flotation charge had the following particle size distribution (after desliming): 16.9%$\leq$25 $\mu$m; 29.7%=25 to 80 $\mu$m; 35.2%=80 to 140 $\mu$m and 18.2%$\geq$140 $\mu$m.

The pH-value of the flotation solution was 9.5, the phosphinylated maleic acid semiesters being present as the sodium salt. A compound according to the invention corresponding to general formula (I) in which $R^2$ is predominantly a $C_{12}$–$C_{14}$ alkyl group (from Example 1(b)) was used in Example 2a and a compound according to the invention corresponding to general formula (I) in which $R^2$ is a $C_{12}$–$C_{16}$ alkyl group (from Example 1(a)) was used in Example 2b. In both cases, mixtures of the mono- and diadducts (formula (I); n=1 and 2) were used as collectors. In both cases, the collector concentration was 3000 g of active substance per ton of ore. The results are set out in Table 1 below.

TABLE 1

| Example | Flotation time minutes | a(*) (%) | b(*) (%) |
|---|---|---|---|
| 2a | 2 | 49 | 25 |
|  | 5 | 77 | 25 |
|  | 12 | 98 | 22 |
| 2b | 2 | 57 | 25 |
|  | 5 | 80 | 26 |
|  | 12 | 86 | 23 |

(*)Explanations:
(a)Metal recovery (in % by weight, based on the charge)
(b)$P_2O_5$—content of the concentrate recovered

RESULT

A high percentage of the phosphate ore was recovered after only a short flotation time, the phosphate content of the ore sample decreasing with increasing flotation time. Toward the end of flotation, the phosphate content of the concentrate recovered was also depleted.

COMPARISON EXAMPLES 1 TO 3

Flotation tests in which sodium oleate (Comparison Example 1), a direct reaction product of maleic acid and hypophosphorous acid (Comparison Example 2) and a non-phosphinylated maleic acid semiester (Comparison Example 3) corresponding to the maleic acid semiester used in Example 2a were carried out under comparable reaction conditions. In each case, the concentration of collector was 300 g of active substance per ton of ore.

The results are shown in Table 2 below.

TABLE 2

| Comparison Example | Flotation time minutes | a(*) % | b(*) % |
|---|---|---|---|
| $C_1$ | 2 | 7 | 18 |
|  | 5 | 21 | 20 |
|  | 12 | 45 | 22 |
| $C_2$ | 2 | No Flotation | |
|  | 5 | No Flotation | |
|  | 12 | No Flotation | |
| $C_3$ | 2 | 27 | 19 |
|  | 5 | 53 | 29 |
|  | 12 | 71 | 31 |

(*)Explanations:
(a)Metal recovery (in % by weight, based on the charge)
(b)$P_2O_5$—content of the concentrate recovered

RESULT

The collectors in Comparison Examples $C_1$ and $C_3$ show considerably poorer performance than the products of general formula (I) according to the invention. Comparison Example $C_3$ in particular shows that it is only by the reaction of the maleic acid semiesters with hypophosphorous acid that products are obtained which have the improved collector properties and this is because the maleic acid semiesters alone preferentially float calcite after a flotation time of only two minutes in the first flotation stage. The maleic acid-phosphorous acid reaction product used in Comparison Example $C_2$ does not show any collector properties at all.

EXAMPLE 3

A low-value cassiterite ore was floated at 20° C. in a 1 liter laboratory flotation cell (Klockner-Humboldt-Deutz Model MN 935/4). A phosphinylated maleic acid semiester corresponding to general formula (I) in which $R^1$ is a $C_{12}$–$C_{14}$ alkyl group (Example 3a) and $R^2$ a $C_{12}$–$C_{16}$ alkyl group (Example 3b) was used as collector in a quantity of 300 g active substance per ton of ore. The cassiterite ore contained essentially granite, tourmaline and magnetite as gangue. The ore was found by analysis to have the following composition: 1.0% $SnO_2$, 58.8% $SiO_2$, 7.1% $Fe_2O_3$.

The flotation charge had the following particle size distribution: 60% ≦25 μm and 40% =25 to 100 μm.

Waterglass was added as depressor in a quantity of 2200 g/t ore and the pH-value of the pulp was adjusted to 5 with sulfuric acid.

The results are shown in Table 3.

COMPARISON EXAMPLE 4 AND 5

The corresponding non-phosphinylated maleic acid semiester starting materials used in Examples 3a and 3b for the production of the compounds of general formula (I) were used as comparison substances; i.e. $C_4$ and $C_5$.

The quantity of comparison substance was 300 g/t ore in both Comparison Example 4 and in Comparison Example 5.

The results are shown with those of Example 3a and 3b in Table 3 which follows:

TABLE 3

| Example and Comparison Example (C) | a(*) (%) | b(*) (%) |
|---|---|---|
| 3a | 91 | 4.2 |
| 3b | 82 | 4.8 |
| $C_4$ | 96 | 2.5 |
| $C_5$ | 94 | 2.5 |

(*)Explanations:
(a)Metal recovery (in % by weight, based on the charge)
(b)$P_2O_5$—content of the concentrate recovered

RESULT

As can be seen from Table 3, the compounds of general formula (I) according to the invention (Examples 3a and 3b) show distinctly higher selectivity for comparable recovery of the valuable mineral than the corresponding non-phosphinylated maleic acid semiesters.

We claim:

1. In the process of concentrating non-sulfidic minerals from ground ores by flotation, the improvement comprising using as a collector in said process from about 10 to about 5000 g/t of ore of at least one monoadduct or diadduct of phosphinic acid with a maleic acid semiester or its salt corresponding to the following formula

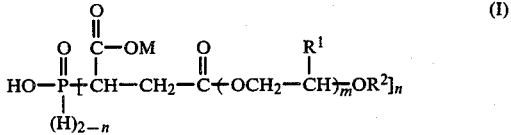

in which
$R^1$ is hydrogen or a methyl group,
$R^2$ is an unsubstituted or hydroxyl substituted $C_8$–$C_{18}$ linear or branched alkyl or cycloalkyl group or an aryl group corresponding to the formula

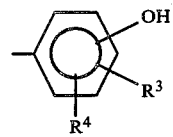

in which
$R^3$ and $R^4$ may be the same or different and are hydrogen or a linear or branched unsubstituted alkyl group, containing from 7 to 12 C-atoms,
M is H, Na, K or $NH_4$,
m is an integer of from 1 to 8, and
n is 1 or 2.

2. The process of claim 1 wherein $R^1$ is hydrogen, $R^2$ is a linear alkyl group containing from 12 to 16 C-atoms, M is Na, K or $NH_4$, and m is an integer of from 2 to 4.

3. The process of claim 1 wherein said at least one monoadduct or diadduct comprises a mixture of a monoadduct and a diadduct.

4. The process of claim 1 wherein the at least one monoadduct or diadduct of formula I is used with an anionic surfactant as a co-collector.

5. The process of claim 1 wherein the at least one monoadduct or diadduct of formula I is employed in a quantity of from about 100 to about 3000 g/t of ore.

* * * * *